(12) United States Patent
Grande et al.

(10) Patent No.: US 10,639,128 B2
(45) Date of Patent: May 5, 2020

(54) SPLINT DEVICE FOR FORMING A FIDUCIAL MARKER FOR A SURGICAL ROBOT GUIDANCE SYSTEM, AND ASSOCIATED METHOD

(71) Applicant: NEOCIS, INC., Miami, FL (US)

(72) Inventors: Federico Grande, Stuart, FL (US); Yohama Lorenzo, Miami Beach, FL (US); Jeffrey Ganeles, Boca Raton, FL (US); Nima Massoomi, San Francisco, CA (US); Alon Mozes, Miami Beach, FL (US); Juan Salcedo, Miami, FL (US)

(73) Assignee: NEOCIS, INC., Miami, FL (US)

( * ) Notice: Subject to any disclaimer, the term of this patent is extended or adjusted under 35 U.S.C. 154(b) by 301 days.

(21) Appl. No.: 15/203,466

(22) Filed: Jul. 6, 2016

(65) Prior Publication Data
US 2016/0310233 A1   Oct. 27, 2016

Related U.S. Application Data

(63) Continuation of application No. PCT/US2015/010329, filed on Jan. 6, 2015.
(Continued)

(51) Int. Cl.
*A61C 1/08*      (2006.01)
*A61B 34/30*    (2016.01)
(Continued)

(52) U.S. Cl.
CPC .............. *A61C 1/084* (2013.01); *A61C 1/082* (2013.01); *A61B 34/30* (2016.02); *A61B 90/16* (2016.02);
(Continued)

(58) Field of Classification Search
CPC ........... A61C 1/084; A61C 1/082; A61C 9/00; A61B 34/30; A61B 2017/00951
(Continued)

(56) References Cited

U.S. PATENT DOCUMENTS 1,367,628 A  *  2/1921  Roach ................. A61C 9/0006
                                                               433/40
2006/0281991 A1    12/2006  Fitzpatrick et al.
(Continued)

FOREIGN PATENT DOCUMENTS

WO    WO 2005/091976 A2    10/2005

*Primary Examiner* — Heidi M Eide
*Assistant Examiner* — Mirayda A Aponte
(74) *Attorney, Agent, or Firm* — Womble Bond Dickinson (US)

(57) ABSTRACT

A method of implementing a splint device, and associated splint device are provided for a guidance system of a surgical robot. An adhesive material is engaged with a first stabilizing portion of a first splint portion, and the adhesive material is engaged with a second stabilizing portion of a second splint portion. The first or second splint portion has a mounting portion extending outwardly therefrom, The first and second splint portions are removably engaged with each other and about a tooth of a patient such that, when engaged, the first stabilizing portion is generally opposed to and laterally spaced apart from the second stabilizing portion to define a channel therebetween, with the mounting portion being disposed and extending outwardly of the channel, and with the first and second stabilizing portions defining the channel being secured to respective sides of the tooth via the adhesive material.

7 Claims, 7 Drawing Sheets

Related U.S. Application Data (60) Provisional application No. 61/923,980, filed on Jan. 6, 2014.

(51) Int. Cl.
| | | |
|---|---|---|
| *A61B 90/00* | (2016.01) | |
| *A61C 9/00* | (2006.01) | |
| *A61B 90/16* | (2016.01) | |
| *A61B 34/20* | (2016.01) | |
| *A61B 17/00* | (2006.01) | |

(52) U.S. Cl.
CPC ............... *A61B 2017/00951* (2013.01); *A61B 2034/2055* (2016.02); *A61B 2090/3983* (2016.02); *A61B 2090/3991* (2016.02); *A61C 9/0006* (2013.01)

(58) Field of Classification Search
USPC ......................................... 433/75, 46, 40, 47
See application file for complete search history.

(56) References Cited

U.S. PATENT DOCUMENTS

| | | |
|---|---|---|
| 2008/0166681 A1 | 7/2008 | Weinstein et al. |
| 2008/0171305 A1 | 7/2008 | Sonenfeld et al. |
| 2013/0131505 A1 | 5/2013 | Daon et al. |

\* cited by examiner

SPLINT DEVICE FOR FORMING A FIDUCIAL MARKER FOR A SURGICAL ROBOT GUIDANCE SYSTEM, AND ASSOCIATED METHOD

CROSS REFERENCE TO RELATED APPLICATIONS

This application is a continuation of International Application No. PCT/US2015/010329, filed Jan. 6, 2015, which International application was published by the International Bureau in English on Jul. 9, 2015, which claims priority to U.S. Provisional Application No. 61/923,980, filed on Jan. 6, 2014, which all are incorporated by reference herein in their entirety.

BACKGROUND

Field of the Disclosure

The present application relates to surgical robots and associated guidance systems and, more particularly, to a splint device for forming a fiducial marker and/or a tracking marker for the guidance system of a surgical robot used, for example, in dental surgery.

Description of Related Art

Robotic systems are being increasingly implemented in surgical applications. One such example involves a surgical robot used in dental surgery. Such robots are often associated with a guidance system used to guide the surgical instrument implemented by the surgical robot. The guidance system may also be configured to be involved in the surgical pre-planning process, whether by being involved in gathering and/or analyzing patient data, and planning the surgical procedure, or by relying upon pre-planning data to guide the surgical instrument to conduct the surgical procedure.

In particular surgical procedures, some surgical robotic systems rely upon a fixed reference point associated with the patient's body for guiding the surgical robot. That is, some such surgical robotic systems define a frame of reference with respect to the patient's body so as to account or otherwise compensate for movements or motion of the patient during the procedure, whether during pre-planning or during the actual surgical procedure itself. This reference point must also be repeatable such that multiple engagements/disengagements (i.e., periods between pre-planning and the actual surgical procedure) do not change the frame of reference implemented by the surgical robot or the guidance system associated therewith.

In particular instances, the reference point (or the connection between the guidance system and the patient to define that reference point) implemented by the guidance system for the surgical robot may be accomplished through, for example, an optical modality, a mechanical modality, an acoustic modality, or other suitable and appropriate tracking/guiding modality, or combination thereof. In some modalities, particularly used in dental surgery applications, one mechanical modality for forming the reference point (i.e., a "fiducial marker") may be accomplished, for example, by attaching/securing a rigid element to the head/teeth of the patient. Such a rigid element, in some instances, may be referred to as and may comprise a splint (see, e.g., prior art in FIGS. 1, 2A, and 2B). Such a splint may generally include, for instance, a retainer portion that grips one or more of the teeth (i.e., by way of an adhesive substance, such as an acrylic material applied between the retainer portion and the teeth), a mounting portion (i.e., mounting arm) that connects the retainer portion to a kinematic mount, and the kinematic mount, itself, which may comprise an attachment point for a tracking portion associated with the guidance system for the surgical robot (i.e., wherein, for instance, reflective markers may be mounted to the attachment point for optical tracking of the fiducial marker, or the attachment point may include a securing site for forming a mechanical connection therewith for mechanical tracking of the fiducial marker, or the attachment point may otherwise be configured to receive an appropriate element associated with any other suitable tracking arrangement for the fiducial marker).

In such instances, it may be preferable for the retainer to be as rigid as possible (i.e., the structure of the retainer itself, as well as the fixation thereof to the teeth of the patient) throughout the surgical procedure. However, it may also be preferable for the retainer to be readily removable when the surgical procedure is complete. In some instances, it may be preferable for the retainer to be reproducibly removed and replaced, for example, between the pre-planning procedure (i.e., a CT scan) which may occur on one day (when the retainer must be in place so the fiducial marker(s) associated therewith are captured in the scan), and the surgical procedure may occur on another day (wherein the surgical procedure requires the retainer to be in place for tracking/guiding the surgical procedure).

Figure 1:
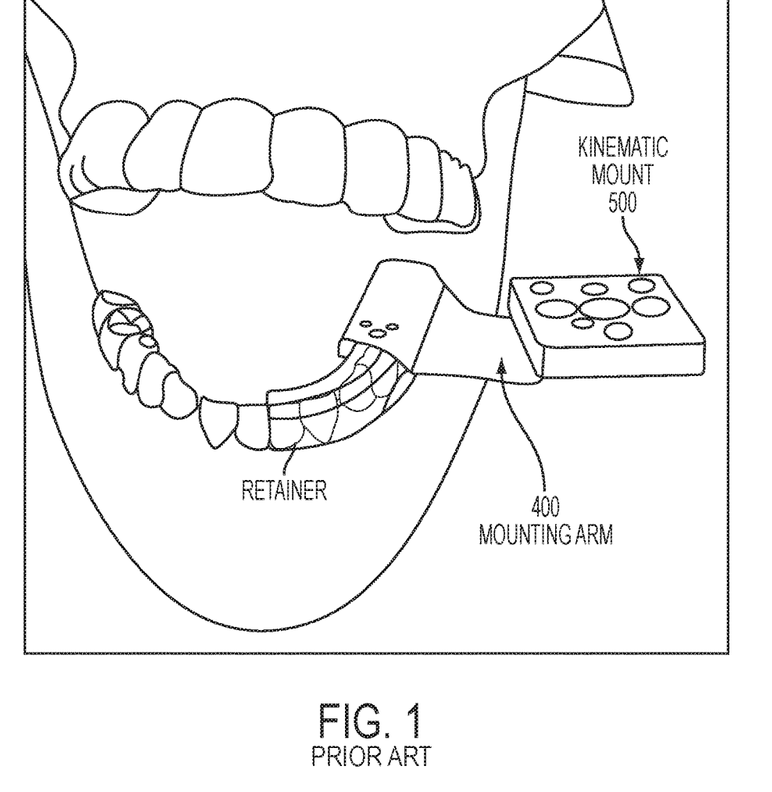
FIG. 1 schematically illustrates a prior art splint device engaged with a representative model of a mouth of a patient so as to provide a fiducial marker and/or a tracking marker for a guidance system for a surgical robot for dental surgeries.
Figure 2A:
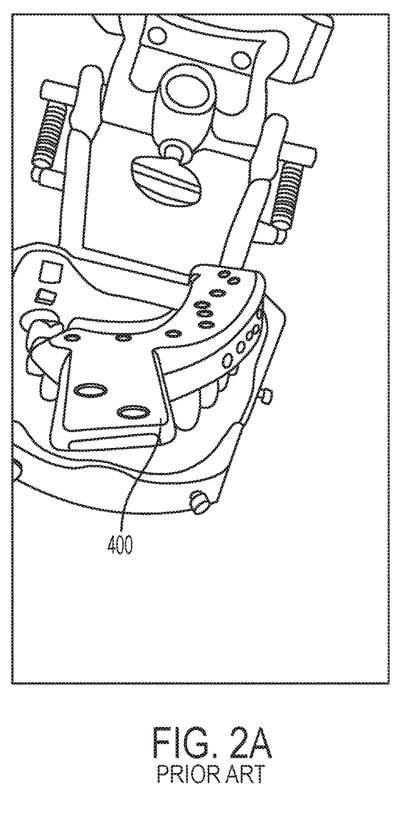
FIGS. 2A and 2B schematically illustrates a prior art splint device engaged with a representative model of a mouth of a patient so as to provide a fiducial marker and/or a tracking marker for a guidance system for a surgical robot for dental surgeries (FIG. 2A) and the prior art splint device disengaged from the representative model of the mouth of the patient (FIG. 2B)
Figure 2B:
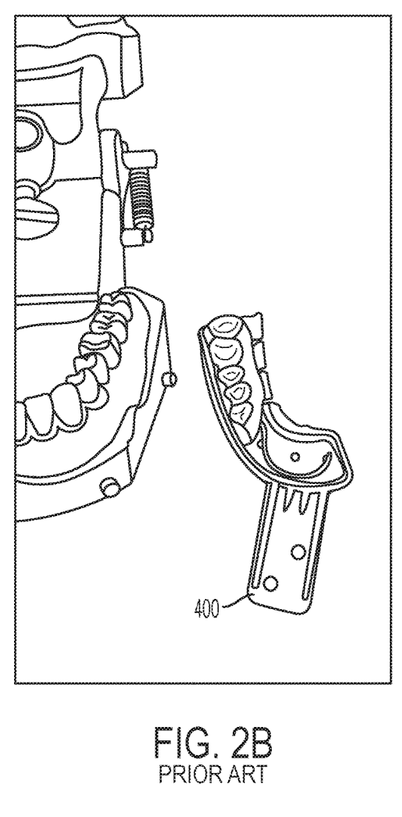

Such prior art splint devices as shown, for example, in FIGS. 1, 2A, and 2B, also require a careful balance of the adhesive material (i.e., dental acrylic) to be applied in order to be effective in rigidly mounting the retainer portion to the teeth of the patient. For instance, if too little of the adhesive material is applied in the retainer portion, the splint device may be too easily separated from the teeth, since the amount of the adhesive material may not be sufficient to bond the retainer to the teeth to sufficiently resist the forces applied thereto during the surgical procedure. However, if too much of the adhesive material is applied to the retainer portion, the excess adhesive material may flows into the tooth undercuts (i.e., the portion of the tooth where the tooth narrows toward the gum-line and/or the spaces between teeth), the retainer portion will not be removable at the end of the surgical procedure, without, for instance, drilling into the solidified adhesive material to remove the retainer portion from the tooth/teeth. In such instances, the retainer portion will likely not be re-usable for the particular patient, and if further procedures are required, a new retainer portion, including a new mounting portion for the fiducial marker and/or tracking marker, may also be required.

As such, there exists a need for a splint device for forming a fiducial marker for the guidance system of a surgical robot used, for example, in dental surgery which addresses these and other limitations of prior art devices.

SUMMARY OF THE DISCLOSURE

The above and other needs are met by aspects of the present disclosure which, in one particular aspect, provides a splint device for use with a guidance system of a surgical robot, for example, for dental surgery. Such a device may comprise a first splint portion having a first stabilizing portion with opposed surfaces, and a second splint portion having a second stabilizing portion with opposed surfaces. A mounting portion is engaged with one of the first and second splint portions and extends outwardly therefrom. The first and second splint portions are removably engageable with each other such that, when engaged, one surface of the first stabilizing portion is generally opposed to and laterally spaced apart from one surface of the second stabilizing portion to define a channel therebetween, with the mounting portion being disposed and extending outwardly of the channel.

Another aspect of the present disclosure provides a method of implementing a splint device for use with a guidance system of a surgical robot, for example, for dental surgery. Such a method comprises engaging an adhesive material with a surface of a first stabilizing portion of a first splint portion, and engaging the adhesive material with a surface of a second stabilizing portion of a second splint portion, wherein one of the first and second splint portions has a mounting portion engaged therewith and extending outwardly therefrom. The first and second splint portions are removably engaged with each other and about a tooth of a patient such that, when engaged, one surface of the first stabilizing portion is generally opposed to and laterally spaced apart from one surface of the second stabilizing portion to define a channel therebetween, with the mounting portion being disposed and extending outwardly of the channel, and with the surfaces of the first and second stabilizing portions defining the channel being secured to respective sides of the tooth via the adhesive material.

The present disclosure thus includes, without limitation, the following example embodiments:

Example Embodiment 1

A splint device for use with a guidance system of a surgical robot for dental surgery, wherein such a device comprises a first splint portion having a first stabilizing portion with opposed surfaces; a second splint portion having a second stabilizing portion with opposed surfaces; and a mounting portion engaged with one of the first and second splint portions and extending outwardly therefrom; wherein the first and second splint portions are removably engageable with each other such that, when engaged, one surface of the first stabilizing portion is generally opposed to and laterally spaced apart from one surface of the second stabilizing portion to define a channel therebetween, with the mounting portion being disposed and extending outwardly of the channel.

Example Embodiment 2

The device of any preceding or subsequent example embodiment, or combinations thereof, wherein one of the first and second splint portions include a partition portion engaged therewith, the partition portion being configured to extend into the channel between the opposed surfaces of the first and second stabilizing portions, upon engagement of the first and second splint portions.

Example Embodiment 3

The device of any preceding or subsequent example embodiment, or combinations thereof, wherein one of the first and second stabilizing portions includes a bridge portion engaged therewith, the bridge portion having opposing ends, the bridge portion having one of the opposed ends thereof engaged with, and extending at least 90 degrees to, the respective one of the first and second stabilizing portions, the other of the opposed ends being configured to engage the other of the first and second stabilizing portions at an angle of at least 90 degrees thereto, such that the first and second stabilizing portions and the bridge portion cooperate to define the channel.

Example Embodiment 4

The device of any preceding or subsequent example embodiment, or combinations thereof, wherein the first stabilizing portion includes a first bridge portion engaged therewith and the second stabilizing portion includes a second bridge portion engaged therewith, each bridge portion having opposing ends, the first bridge portion having one of the opposed ends thereof engaged with, and extending at least 90 degrees to, the first stabilizing portion, and the second bridge portion having one of the opposed ends thereof engaged with, and extending s at least 90 degrees to, the second stabilizing portion, the respective others of the opposed ends of the first and second bridge portions being configured to complementarily engage each other, such that the first and second stabilizing portions and the first and second bridge portions cooperate to define the channel.

Example Embodiment 5

The device of any preceding or subsequent example embodiment, or combinations thereof, wherein the first and second splint portions are removably engageable with each other about respective first ends of the first and second stabilizer portions, the first and second stabilizer portions diverging from the respective first ends toward respective second ends thereof.

Example Embodiment 6

A method of implementing a splint device for use with a guidance system of a surgical robot for dental surgery, wherein such a method comprises engaging an adhesive material with a surface of a first stabilizing portion of a first splint portion; engaging the adhesive material with a surface of a second stabilizing portion of a second splint portion, one of the first and second splint portions having a mounting portion engaged therewith and extending outwardly therefrom; and removably engaging the first and second splint portions with each other and about a tooth of a patient such that, when engaged, one surface of the first stabilizing portion is generally opposed to and laterally spaced apart from one surface of the second stabilizing portion to define a channel therebetween, with the mounting portion being disposed and extending outwardly of the channel, and with the surfaces of the first and second stabilizing portions defining the channel being secured to respective sides of the tooth via the adhesive material.

Example Embodiment 7

The method of any preceding or subsequent example embodiment, or combinations thereof, wherein one of the first and second splint portions include a partition portion engaged therewith, the partition portion being configured to extend into the channel between the opposed surfaces of the first and second stabilizing portions, upon engagement of the first and second splint portions, and removably engaging the first and second splint portions with each other further comprises removably engaging the first and second splint portions with each other such that the partition portion separates the adhesive material engaged with the surface of the first stabilizing portion from the adhesive material engaged with the surface of the second stabilizing portion.

Example Embodiment 8

The method of any preceding or subsequent example embodiment, or combinations thereof, wherein one of the first and second stabilizing portions includes a bridge portion engaged therewith, the bridge portion having opposing ends, the bridge portion having one of the opposed ends thereof engaged with, and extending at least 90 degrees to, the respective one of the first and second stabilizing portions, the other of the opposed ends being configured to engage the other of the first and second stabilizing portions at an angle of at least 90 degrees thereto, such that the first and second stabilizing portions and the bridge portion cooperate to define the channel, and wherein removably engaging the first and second splint portions with each other further comprises removably engaging the first and second splint portions with each other such that the bridge portion engages only the adhesive material engaged with the surface of the one of the first and second stabilizing portions engaged therewith.

Example Embodiment 9

The method of any preceding or subsequent example embodiment, or combinations thereof, wherein the first stabilizing portion includes a first bridge portion engaged therewith and the second stabilizing portion includes a second bridge portion engaged therewith, each bridge portion having opposing ends, the first bridge portion having one of the opposed ends thereof engaged with, and extending at least 90 degrees to, the first stabilizing portion, and the second bridge portion having one of the opposed ends thereof engaged with, and extending at least 90 degrees to, the second stabilizing portion, the respective others of the opposed ends of the first and second bridge portions being configured to complementarily engage each other, such that the first and second stabilizing portions and the first and second bridge portions cooperate to define the channel, and wherein removably engaging the first and second splint portions with each other further comprises removably engaging the first and second stabilizing portions with each other such that the first bridge portion engages only the adhesive material engaged with the surface of the first stabilizing portions engaged therewith and such that the second bridge portion engages only the adhesive material engaged with the surface of the second stabilizing portions engaged therewith.

These and other features, aspects, and advantages of the present disclosure will be apparent from a reading of the following detailed description together with the accompanying drawings, which are briefly described below. The present disclosure includes any combination of two, three, four, or more features or elements set forth in this disclosure, regardless of whether such features or elements are expressly combined or otherwise recited in a specific embodiment description herein. This disclosure is intended to be read holistically such that any separable features or elements of the disclosure, in any of its aspects and embodiments, should be viewed as intended, namely to be combinable, unless the context of the disclosure clearly dictates otherwise.

It will be appreciated that the summary herein is provided merely for purposes of summarizing some example aspects so as to provide a basic understanding of the disclosure. As such, it will be appreciated that the above described example aspects are merely examples and should not be construed to narrow the scope or spirit of the disclosure in any way. It will be appreciated that the scope of the disclosure encompasses many potential aspects, some of which will be further described below, in addition to those herein summarized. Further, other aspects and advantages of such aspects disclosed herein will become apparent from the following detailed description taken in conjunction with the accompanying drawings which illustrate, by way of example, the principles of the described aspects.

BRIEF DESCRIPTION OF THE SEVERAL VIEWS OF THE DRAWING(S)

Having thus described the disclosure in general terms, reference will now be made to the accompanying drawings, which are not necessarily drawn to scale, and wherein:

DETAILED DESCRIPTION OF THE DISCLOSURE

The present disclosure now will be described more fully hereinafter with reference to the accompanying drawings, in which some, but not all aspects of the disclosure are shown. Indeed, the disclosure may be embodied in many different forms and should not be construed as limited to the aspects set forth herein; rather, these aspects are provided so that this disclosure will satisfy applicable legal requirements. Like numbers refer to like elements throughout.

Figure 3A:
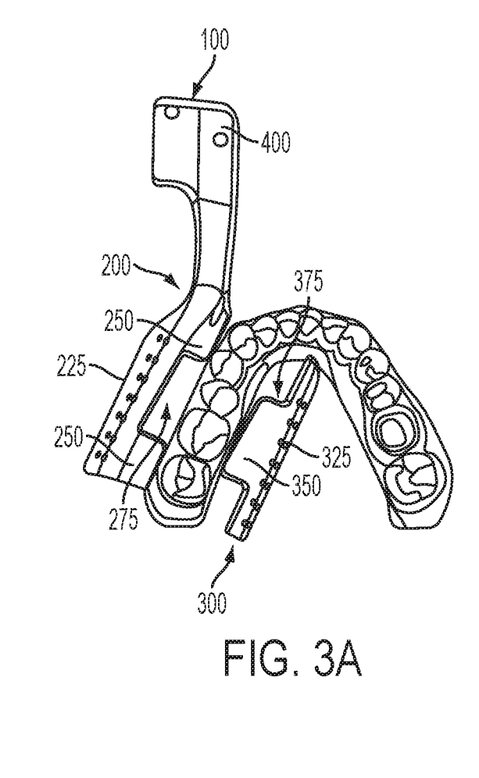
FIGS. 3A and 3B schematically illustrates a pre-assembly view of a splint device in relation to a representative model of a mouth of a patient (FIG. 3A) and the splint device assembled and engaged with the representative model of the mouth of the patient so as to provide a fiducial marker and/or a tracking marker for a guidance system for a surgical robot for dental surgeries (FIG. 3B), according to one aspect of the present disclosure.
Figure 3B:
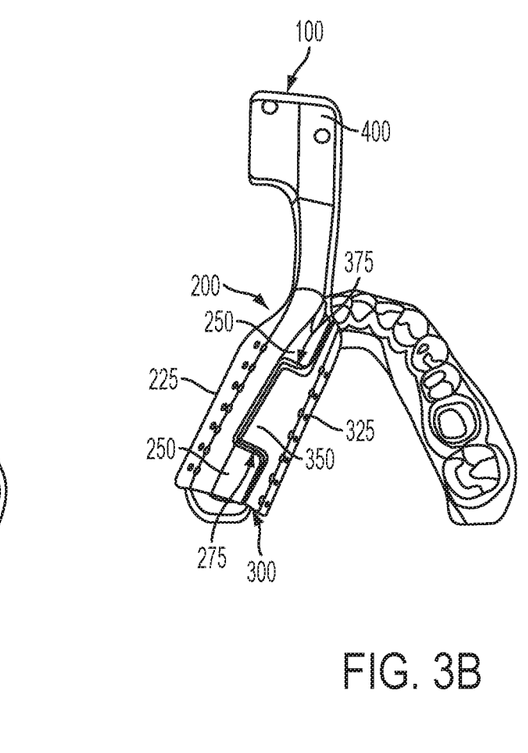

Particular aspects of the present disclosure, as shown, for example, in FIGS. 3A and 3B provide a splint device 100 for use with a guidance system of a surgical robot, for instance, for dental surgery. One skilled in the art, however, will appreciate that the concept of the splint device disclosed herein as forming a fiducial marker and/or a tracking marker, or otherwise a frame of reference for a surgical robotic system may find applicability to other surgical processes not involving dental surgery, such as, for example, orthopedic surgery, ENT surgery, and neurosurgery. As such, the aspects of the disclosure presented herein are merely examples of the applicability of the disclosed concepts and are not intended to be limiting in any manner.

Figure 5:
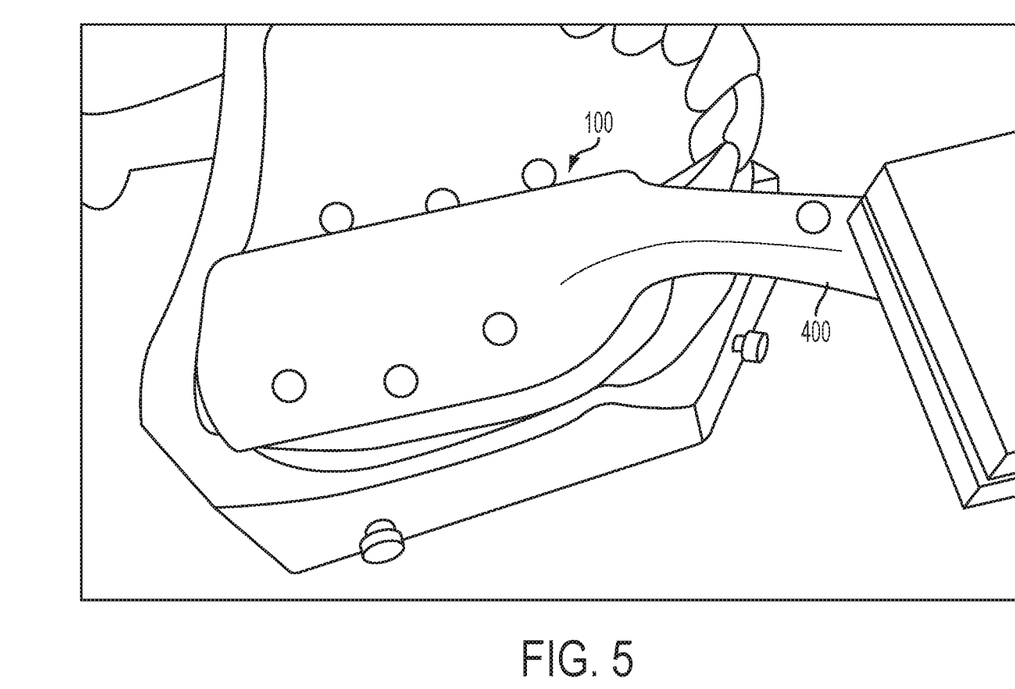
FIG. 5 schematically illustrates an assembled splint device engaged with a representative model of a mouth of a patient, for providing a fiducial marker and/or a tracking marker for a guidance system for a surgical robot for dental surgeries, according to one aspect of the present disclosure.

Such a splint device 100 may comprise, for example, a first splint portion 200 having a first stabilizing portion 225 with opposed surfaces 225A, 225B, and a second splint portion 300 having a second stabilizing portion 325 with opposed surfaces 325A, 325B. A mounting portion 400 may be engaged with one of the first and second splint portions 200, 300 and, in particular aspects, the mounting portion 400 may be further configured to extend outwardly from the first or second splint portion 200, 300. That is, the mounting portion 400 (i.e., mounting arm) may extend from the first and/or second splint portion (i.e., from either splint portion, or from both splint portions via cooperation therebetween) 200, 300, and may connect the first and/or second splint portions 200, 300 to a kinematic mount 500 (see, e.g., FIGS. 1 and 5). As previously discussed herein, the kinematic mount 500, itself, may comprise an attachment point for a tracking portion (or tracking arm or other tracking provision) associated with the guidance system for the surgical robot (i.e., wherein, for instance, reflective markers may be mounted to the attachment point for optical tracking of the fiducial marker or the splint device itself, or the attachment point may include a securing site for forming a mechanical connection therewith for mechanical tracking of the fiducial marker, or the attachment point may otherwise be configured to receive an appropriate element associated with any other suitable tracking arrangement for the fiducial marker). In other aspects, the kinematic mount 500 may be configured or otherwise arranged to function as a fixed mounting site for particular tracking devices such as, for example, one or more markers that may be permanently affixed to the kinematic mount 500 and configured to be trackable by an optical-type tracking device (i.e., an optical tracking marker).

In some aspects, as shown, for example, in FIGS. 3A and 3B, the first and second splint portions 200, 300 are removably engageable with each other such that, when engaged (see, e.g., FIG. 3B), one surface (i.e., 225B) of the first stabilizing portion 225 is generally opposed to and laterally spaced apart from one surface (i.e., 325A) of the second stabilizing portion 325 to define a channel 600 therebetween. The channel 600 may generally be in the form of, for example, a "U" channel or an inverted "U" channel, as appropriate or desirable for mounting, for example, to the mouth/teeth of a patient. For example, an inverted "U" channel may be applicable to the lower jaw or lower teeth of a patient, while a "U" channel may be applicable to the upper jaw or upper teeth of a patient. Upon being mounted to the mouth/teeth of the patient, the mounting portion 400 is disposed externally to the channel 600 and extends outwardly of the channel 600. The splint portions 200, 300, upon engagement, may be secured together in any suitable manner such as, for example, using pins, fasteners, clips, and/or the like, as will be appreciated by one skilled in the art.

In some aspects, as shown, for example, in FIGS. 3A, 3B, 4A, and 4B, the first stabilizing portion 225 may include a first bridge portion 250 engaged therewith, and the second stabilizing portion 325 may include a second bridge portion 350 engaged therewith. Each bridge portion includes opposing ends, wherein the first bridge portion 250 has one of the opposed ends thereof engaged with the first stabilizing portion 225 and extends at least 90 degrees with respect thereto, and the second bridge portion 350 has one of the opposed ends thereof engaged with the second stabilizing portion 325 and extends at least 90 degrees with respect thereto. As shown, for example, in FIGS. 3A and 3B, the respective others of the opposed ends of the first and second bridge portions 250, 350 may be configured to complementarily engage each other, such that the first and second stabilizing portions 225, 325 and the first and second bridge portions 250, 350 cooperate to define the channel 600. In some aspects, for example, where the first stabilizing portion 225 extends at least 90 degrees with respect to the first bridge portion 250, and the second stabilizing portion 325 extends at least 90 degrees with respect to the second bridge portion 350, the first and second stabilizer portions 225, 325 thus diverge from the respective first ends thereof engaged with the first and second bridge portion 250, 350, toward respective free or unattached second ends thereof. One skilled in the art will appreciate, however, that the engagement angle between the respective stabilizing portion and the corresponding bridge portion may vary as necessary or desired, according to the aspects of the present disclosure herein. For example, the engagement angle between the stabilizing portion and the corresponding bridge portion of one of the first and second splint portions may not necessarily be the same as the engagement angle between the stabilizing portion and the corresponding bridge portion of the other of the first and second splint portions. In other instances, the engagement angle between the stabilizing portion and the corresponding bridge portion of either splint portion may be about 90 degrees or less than 90 degrees.

The channel 600 may extend lengthwise, for example, over one tooth or over a plurality of teeth in the mouth of the patient. As shown in FIGS. 3A and 3B, the channel 600 may extend over a plurality of teeth in the mouth of the patient. In such aspects, the first and second bridge portions 250, 350, may include for example, alignment elements to promote or facilitate the complementary engagement therebetween for assembly of the splint device 100. For example, the second bridge portion 350 may include a protrusion 375, while the first bridge portion 250 may define a groove 275 configured to receive the protrusion 375 of the second bridge portion 375. Engagement between the protrusion 375 and the groove 275 may thus cause the bridge portions 250, 350 to align such that the stabilizing portions 225, 325 are opposed to each other in a particular alignment to define the channel 600.

One skilled in the art will appreciate, however, that the first and second stabilizing portions 225, 325 may be configured to be engaged in different manners. For example, in some aspects, one of the first and second stabilizing portions 225, 325 may include a bridge portion (not shown) engaged therewith, wherein such a bridge portion may have opposing ends. In such instances, the bridge portion may have one of the opposed ends thereof engaged with the one of the first and second stabilizing portions 225, 325, and be arranged to extend at an angle of at least 90 degrees to the one of the first and second stabilizing portions 225, 325. Accordingly, the other of the opposed ends of the bridge portion is configured to engage the other of the first and second stabilizing portions 225, 325, at an angle of at least 90 degrees in relation thereto, such that the first and second stabilizing portions 225, 325 and the bridge portion cooperate to define the channel 600 (i.e., the bridge portion extends only from one of the first and second stabilizing portions 225, 325, and the free end of the bridge portion is configured for complementary engagement directly with the other of the first and second stabilizing portions 225, 325.

In some aspects of the present disclosure, the removably engaged splint portions 200, 300, when engaged to form the splint device 100, may cooperate to perform a similar function as associated with prior art splint devices. More particularly, the splint device 100 formed through engagement of the first and second splint portions 200, 300, may be configured to define a channel 600 that is further configured to receive an adhesive material therein so as to facilitate engagement with and adherence to a structure such as, for example, the teeth of a patient. However, one particular advantage of aspects of the present disclosure is that, when it is desirable to remove the splint device 100 from the mouth of the patient, the first and second splint portions 200, 300 may be disengaged from each other, and individually removed, without the limitations of prior art splint devices. For example, even if more of the adhesive material (i.e., dental acrylic) than necessary is used to secure the splint device 100 to the teeth of the patient, and such excess adhesive material has flowed into the tooth undercuts (i.e., the portion of the tooth where the tooth narrows toward the gum-line and/or the spaces between teeth), the first and second splint portions 200, 300 may be disengaged to allow removal of the splint device 100, without, for instance, drilling into the solidified adhesive material to remove the splint device from the tooth/teeth, as generally required with prior art splint devices. That is, even if excess dental acrylic has flowed lower down on the teeth than generally necessary or desirable, the splint portions 200, 300 of the splint device 100 may still be readily separated and removed at the end of the procedure.

Figure 4A:
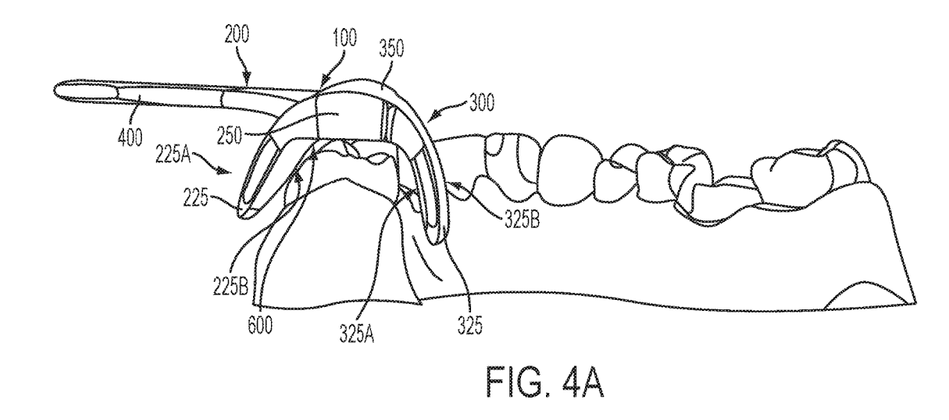
FIGS. 4A and 4B schematically illustrates elevations of a splint device in relation to a representative model of a mouth of a patient, for providing a fiducial marker and/or a tracking marker for a guidance system for a surgical robot for dental surgeries, according to one aspect of the present disclosure.
Figure 4B:
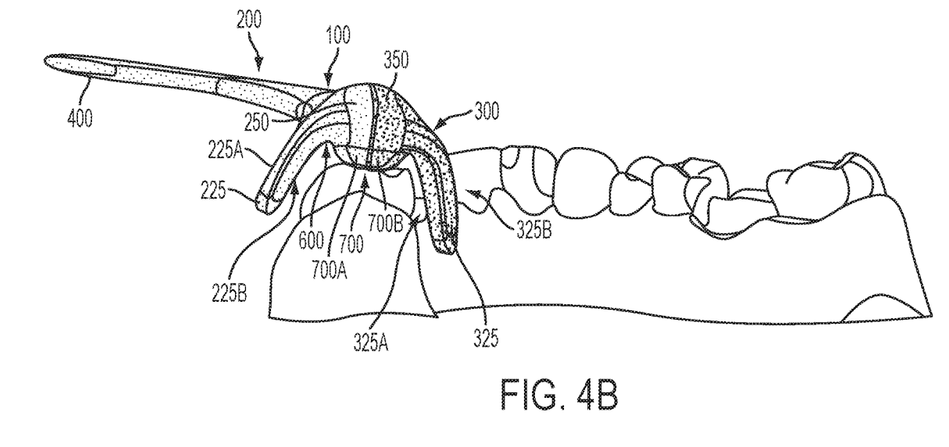

In some aspects, the enhanced removability of the separable or removably engaged splint portions 200, 300 may be further enhanced, for example, if the portion of the adhesive material securing the first splint portion 200 to the tooth/teeth is kept separate from the portion of the adhesive material securing the second splint portion 300 to the tooth/teeth. As such, in some particular aspects, one of the first and second splint portions 200, 300 may include a partition portion 700 engaged therewith, wherein the partition portion 700 may be arranged and configured to extend into the channel 600, between the opposed surfaces of the first and second stabilizing portions 225, 325, upon engagement of the first and second splint portions 200, 300 (see, e.g., FIG. 4B). In such instances, the partition portion 700 functions as a divider for the channel 600, generally extending along all or part of the length thereof and dividing the channel 600 into two lengthwise portions or separate lengthwise channels. In some instances, it may be further advantageous for the partition portion to be associated with and correspond to the engagement between the first and second splint portions 200, 300. That is, the intended functionality of the partition portion 700 is to establish and/or maintain separation of the portion of the adhesive material securing the first splint portion 200 to the tooth/teeth from the portion of the adhesive material securing the second splint portion 300 to the tooth/teeth. In one example, as shown in FIG. 4B, the partition portion 700 may be divided into two complementary elements 700A, 700B, wherein one element 700A may be configured as a lip or flange extending along the free end or edge of the first bridge portion 250, while the other element 700B may be configured as a lip or flange extending along the free end or edge of the second bridge portion 350. In such instances, the lip/flange may also be configured to conform to the configuration of the respective protrusion 375 or groove 275.

Figure 6:
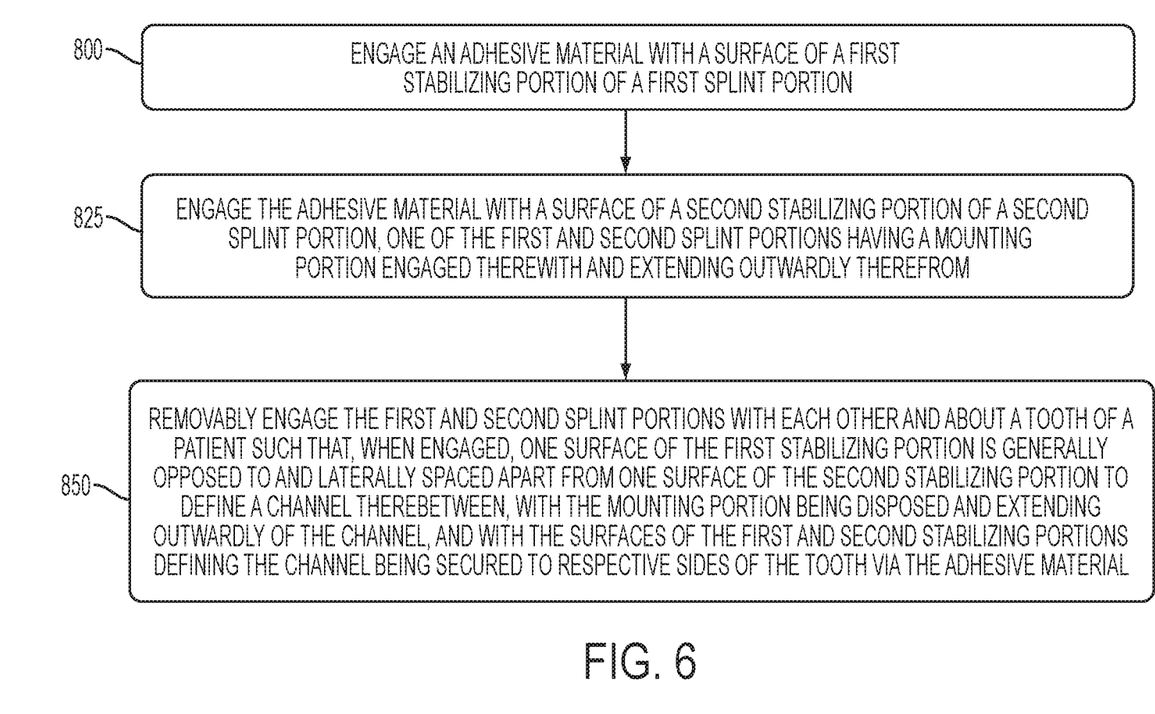
FIG. 6 schematically illustrates a method of implementing a splint device for use with a guidance system of a surgical robot, for example, for dental surgery, according to one aspect of the present disclosure.

Still another aspect of the present disclosure may comprise a method of implementing a splint device for use with a guidance system of a surgical robot, for example, for dental surgery (see, e.g., FIG. 6). Such a method may comprise engaging an adhesive material with a surface of a first stabilizing portion of a first splint portion (block 800), and engaging the adhesive material with a surface of a second stabilizing portion of a second splint portion, wherein one of the first and second splint portions has a mounting portion engaged therewith and extending outwardly therefrom (block 825). The first and second splint portions are then removably engaged with each other and about a tooth of a patient such that, when engaged, one surface of the first stabilizing portion is generally opposed to and laterally spaced apart from one surface of the second stabilizing portion to define a channel therebetween, with the mounting portion being disposed and extending outwardly of the channel, and with the surfaces of the first and second stabilizing portions defining the channel being secured to respective sides of the tooth via the adhesive material (block 850).

Further, in some instances, the first stabilizing portion may include a first bridge portion engaged therewith, and the second stabilizing portion may include a second bridge portion engaged therewith, with each bridge portion having opposing ends. The first bridge portion may have one of the opposed ends thereof engaged with, and extending at least 90 degrees to, the first stabilizing portion, and the second bridge portion may have one of the opposed ends thereof engaged with, and extending at least 90 degrees to, the second stabilizing portion. The respective others of the opposed ends of the first and second bridge portions are also configured to complementarily engage each other, such that the first and second stabilizing portions and the first and second bridge portions thereby cooperate to define the channel. In such instances, removably engaging the first and second splint portions with each other further comprises removably engaging the first and second stabilizing portions with each other such that the first bridge portion engages only the adhesive material engaged with the surface of the first stabilizing portions engaged therewith, and such that the second bridge portion engages only the adhesive material engaged with the surface of the second stabilizing portions engaged therewith In other instances, one of the first and second stabilizing portions may include a bridge portion engaged therewith, with the bridge portion having opposing ends. The bridge portion may have one of the opposed ends thereof engaged with, and extending at least 90 degrees to, the respective one of the first and second stabilizing portions, with the other of the opposed ends being configured to engage the other of the first and second stabilizing portions at an angle of at least 90 degrees in relation thereto, such that the first and second stabilizing portions and the bridge portion thereby cooperate to define the channel. In such instances, removably engaging the first and second splint portions with each other further comprises removably engaging the first and second splint portions with each other such that the bridge portion engages only the adhesive material engaged with the surface of the one of the first and second stabilizing portions engaged therewith.

In yet other aspects, one of the first and second splint portions may include a partition portion engaged therewith, with the partition portion being configured to extend into the channel between the opposed surfaces of the first and second stabilizing portions, upon engagement of the first and second splint portions. In such instances, removably engaging the first and second splint portions with each other further comprises removably engaging the first and second splint portions with each other such that the partition portion separates the adhesive material engaged with the surface of the first stabilizing portion from the adhesive material engaged with the surface of the second stabilizing portion.

Figure 7:
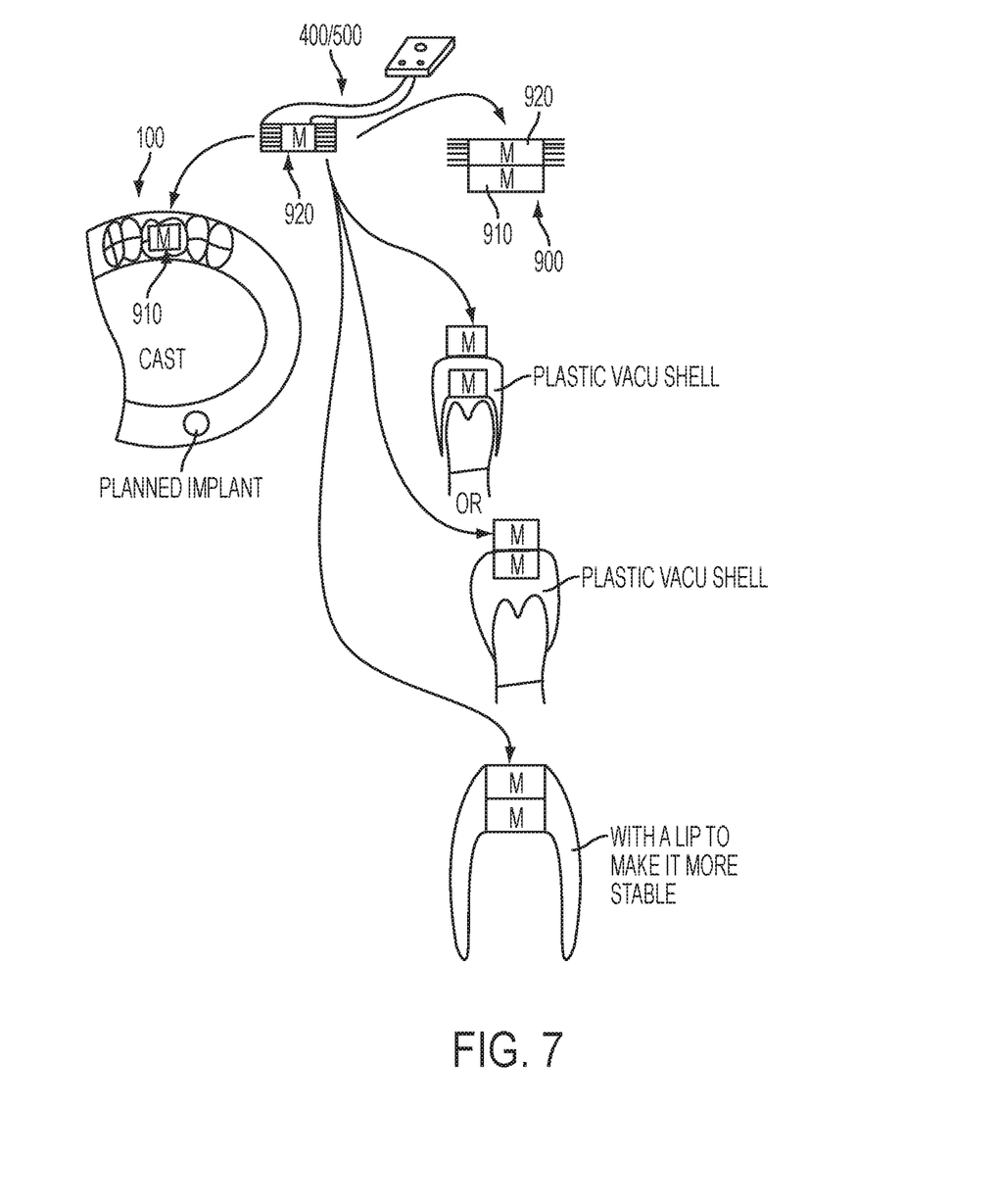
FIG. 7 schematically illustrates a molded polymeric splint device incorporating one portion of an engagement arrangement and a mounting portion/kinematic mount incorporating a complementary portion of the engagement arrangement, so as to provide a re-usable mounting portion/kinematic mount associated with a splint device, according to another aspect of the present disclosure.

In still further aspects of the present disclosure as shown, for example, in FIG. 7, the splint device 100 (or "retainer portion" of the disclosed device having the mounting portion 400 (or mounting arm) and/or the kinematic mount 500 engaged therewith) may comprise custom-molded arrangement comprised of a polymeric material (i.e., an acrylic or other suitable polymer). In some aspects, the splint device 100 may be molded to form the at least two-splint portion configuration otherwise disclosed herein. In other aspects, as necessary or desired, the splint portion 100 (retainer portion) may be molded as a single integral element. In either instance, the splint device 100 may be molded from the selected polymer using, for example, a vacuum sealing or vacuum molding process implementing a rigid (i.e., stone or plaster) model (or basis of the mold) of the structure of the patient to which the splint device 100 is to be affixed.

Further, in either instance, aspects of the present disclosure involve the molded polymeric splint device 100 incorporating one portion 910 of an engagement arrangement 900 and a mounting portion 400/kinematic mount 500 incorporating a complementary portion 920 of the engagement arrangement 900, so as to provide a re-usable mounting portion 400/kinematic mount 500 associated with the molded splint device 100. For example, the engagement arrangement may comprise a screw/nut or other complementary fastener configuration, wherein either of the screw/nut may be molded into the polymeric splint device 100, while the other of the screw/nut may be associated with the mounting portion 400/kinematic mount 500. If the splint device 100 involves a two-splint portion configuration, the one portion 910 of the engagement arrangement 900 may comprise, for instance a nut molded into the protrusion of the second bridge portion. One skilled in the art will appreciate, however, that the one portion 910 of the engagement arrangement 900 may be incorporated into the splint device 100 in many different manners, and in many different locations associated with the molded polymeric splint device 100, and may be configure in many different manners. For example, in some aspects, a "nut" portion may not be necessary, but a threaded orifice may instead be provided in the polymeric splint device 100 or the mounting portion 400/kinematic mount 500. In still other instances, the "screw" portion may not be, for example, molded into the polymeric splint device 100, but instead, the splint device 100 may define an orifice configured to receive the "screw" portion therethrough for engagement with the "nut" portion or threaded orifice associated with the mounting portion 400/kinematic mount 500. In yet further instances, the engagement between the splint device 100 and the mounting portion 400/kinematic mount 500 may include alignment provisions to ensure proper alignment between the splint device 100 and the mounting portion 400/kinematic mount 500, upon engagement therebetween.

Also, in other aspects, the one portion 910 of the engagement arrangement 900 may comprise a first magnetic element, while the complementary portion 920 of the engagement arrangement 900 may comprise a second magnetic element associated with the mounting portion 400/kinematic mount 500. Either magnetic element may comprise, for example, a magnet or a magnetically-attractive material such as a metal. Such a configuration may allow, for instance, for the mounting portion 400/kinematic mount 500 to be re-usable and the splint device 100/retainer portion to be disposable. The one portion 910 of the engagement arrangement 900 may be incorporated into the molded polymeric splint device 100, for instance, in an "overmolding" process, as will be appreciated by one skilled in the art.

Many modifications and other embodiments of the inventions set forth herein will come to mind to one skilled in the art to which these disclosed embodiments pertain having the benefit of the teachings presented in the foregoing descriptions and the associated drawings. For example, the splint device 100, whether molded as a single piece or as two or more complementary pieces, may further be configured to roughly or approximately follow or conform to the tooth/teeth of the patient, including undercuts (i.e., the portion of the tooth where the tooth narrows toward the gum-line and/or the spaces between teeth) if necessary, wherein the lip, flange, or contour formed thereby in the splint device to conform to the tooth/teeth may facilitate stability of the splint device with respect to the corresponding structure of the patient (see, e.g., FIG. 7). Therefore, it is to be understood that embodiments of the invention are not to be limited to the specific embodiments disclosed and that modifications and other embodiments are intended to be included within the scope of the invention. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the disclosure. In this regard, for example, different combinations of elements and/or functions than those explicitly described above are also contemplated within the scope of the disclosure. Although specific terms are employed herein, they are used in a generic and descriptive sense only and not for purposes of limitation.

It should be understood that although the terms first, second, etc. may be used herein to describe various steps or calculations, these steps or calculations should not be limited by these terms. These terms are only used to distinguish one operation or calculation from another. For example, a first calculation may be termed a second calculation, and, similarly, a second step may be termed a first step, without departing from the scope of this disclosure. As used herein, the term "and/or" and the "/" symbol includes any and all combinations of one or more of the associated listed items.

As used herein, the singular forms "a", "an" and "the" are intended to include the plural forms as well, unless the context clearly indicates otherwise. It will be further understood that the terms "comprises", "comprising", "includes", and/or "including", when used herein, specify the presence of stated features, integers, steps, operations, elements, and/or components, but do not preclude the presence or addition of one or more other features, integers, steps, operations, elements, components, and/or groups thereof. Therefore, the terminology used herein is for the purpose of describing particular embodiments only and is not intended to be limiting.

That which is claimed:

1. A splint device for use with a guidance system of a surgical robot for dental surgery, said device comprising:
   a first splint portion having a first stabilizing portion with inner and outer surfaces;

a second splint portion having a second stabilizing portion with inner and outer surfaces;

a mounting portion engaged with one of the first and second splint portions and extending outwardly therefrom; and a partition portion engaged with one of the first and second splint portion, wherein the first and second splint portions are removably engageable with each other such that, when engaged, the inner surface of the first stabilizing portion is generally opposed to and laterally spaced apart from the inner surface of the second stabilizing portion to define a U channel or an inverted U channel therebetween, the inner surface of the first stabilizing portion and the inner surface of the second stabilizing portion defining the U channel or the inverted U channel being adapted to be secured to respective sides of the tooth or the jaw via an adhesive material, the partition portion being configured to extend into the U channel or the inverted U channel, between the inner surfaces of the first and second stabilizing portions, such that the partition portion keeps the adhesive material engaged with the inner surface of the first stabilizing portion separated from the adhesive material engaged with the inner surface of the second stabilizing portion, with the mounting portion being disposed and extending outwardly of the U channel or the inverted U channel.

2. The device of claim 1, wherein one of the first and second stabilizing portions includes a bridge portion engaged therewith, the bridge portion having opposing ends, the bridge portion having one of the opposed ends thereof engaged with, and extending at least 90 degrees to, the respective one of the first and second stabilizing portions, the other of the opposed ends being configured to engage the other of the first and second stabilizing portions at an angle of at least 90 degrees thereto, such that the first and second stabilizing portions and the bridge portion cooperate to define the U channel or the inverted U channel.

3. The device of claim 1, wherein the first stabilizing portion includes a first bridge portion engaged therewith and the second stabilizing portion includes a second bridge portion engaged therewith, each bridge portion having opposing ends, the first bridge portion having one of the opposed ends thereof engaged with, and extending at least 90 degrees to, the first stabilizing portion, and the second bridge portion having one of the opposed ends thereof engaged with, and extending at least 90 degrees to, the second stabilizing portion, the respective others of the opposed ends of the first and second bridge portions being configured to complementarily engage each other, such that the first and second stabilizing portions and the first and second bridge portions cooperate to define the U channel or the inverted U channel.

4. The device of claim 1, wherein the first and second splint portions are removably engageable with each other about respective first ends of the first and second stabilizer portions, the first and second stabilizer portions diverging from the respective first ends toward respective second ends thereof.

5. A method of implementing a splint device for use with a guidance system of a surgical robot for dental surgery, said method comprising:

engaging an adhesive material with a surface of a first stabilizing portion of a first splint portion;

engaging the adhesive material with a surface of a second stabilizing portion of a second splint portion, one of the first and second splint portions including a partition portion engaged therewith, and one of the first and second splint portions having a mounting portion engaged therewith and extending outwardly therefrom; and removably engaging the first and second splint portions with each other and about a tooth or a jaw of a patient such that, when engaged, the surface of the first stabilizing portion is generally opposed to and laterally spaced apart from the surface of the second stabilizing portion to define a U channel or an inverted U channel therebetween, and the partition portion is configured to extend into the U channel or inverted U channel between the opposed surfaces of the first and second stabilizing portions, with the mounting portion being disposed and extending outwardly of the U channel or the inverted U channel, with the surfaces of the first and second stabilizing portions defining the U channel or the inverted U channel being secured to respective sides of the tooth or the jaw via the adhesive material, and with the partition portion keeping the adhesive material engaged with the surface of the first stabilizing portion separated from the adhesive material engaged with the surface of the second stabilizing portion.

6. The method of claim 5, wherein one of the first and second stabilizing portions includes a bridge portion engaged therewith, the bridge portion having opposing ends, the bridge portion having one of the opposed ends thereof engaged with, and extending at least 90 degrees to, the respective one of the first and second stabilizing portions, the other of the opposed ends being configured to engage the other of the first and second stabilizing portions at an angle of at least 90 degrees thereto, such that the first and second stabilizing portions and the bridge portion cooperate to define the U channel or inverted U channel, and wherein removably engaging the first and second splint portions with each other further comprises removably engaging the first and second splint portions with each other such that the bridge portion engages only the adhesive material engaged with the surface of the one of the first and second stabilizing portions engaged therewith.

7. The method of claim 5, wherein the first stabilizing portion includes a first bridge portion engaged therewith and the second stabilizing portion includes a second bridge portion engaged therewith, each bridge portion having opposing ends, the first bridge portion having one of the opposed ends thereof engaged with, and extending at least 90 degrees to, the first stabilizing portion, and the second bridge portion having one of the opposed ends thereof engaged with, and extending at least 90 degrees to, the second stabilizing portion, the respective others of the opposed ends of the first and second bridge portions being configured to complementarily engage each other, such that the first and second stabilizing portions and the first and second bridge portions cooperate to define the U channel or inverted U channel, and wherein removably engaging the first and second splint portions with each other further comprises removably engaging the first and second stabilizing portions with each other such that the first bridge portion engages only the adhesive material engaged with the surface of the first stabilizing portions engaged therewith and such that the second bridge portion engages only the adhesive material engaged with the surface of the second stabilizing portions engaged therewith.

* * * * *